(12) United States Patent
Beeckler

(10) Patent No.: US 9,949,821 B2
(45) Date of Patent: Apr. 24, 2018

(54) COLORED SILICONE FOR IMPLANT SAFETY

(71) Applicant: Biosense Webster (Israel) Ltd., Yokneam (IL)

(72) Inventor: Christopher Thomas Beeckler, Brea, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 111 days.

(21) Appl. No.: 14/978,577

(22) Filed: Dec. 22, 2015

(65) Prior Publication Data

US 2017/0172726 A1  Jun. 22, 2017

(51) Int. Cl.
*A61F 2/12* (2006.01)

(52) U.S. Cl.
CPC .......... *A61F 2/12* (2013.01); *A61F 2240/001* (2013.01); *A61F 2250/0003* (2013.01); *A61F 2250/005* (2013.01); *A61F 2250/008* (2013.01); *A61F 2250/0087* (2013.01); *A61F 2250/0097* (2013.01)

(58) Field of Classification Search
CPC ........................................................ A61F 2/12
USPC ........................................................ 623/7–8
See application file for complete search history.

(56) References Cited

U.S. PATENT DOCUMENTS

| 7,736,391 B2 | 6/2010 | Schwibner et al. |
| 2005/0142162 A1 | 6/2005 | Hunter et al. |
| 2005/0187624 A1* | 8/2005 | Corbitt, Jr. ................ A61F 2/12 623/8 |
| 2009/0157180 A1* | 6/2009 | Schraga .................. A61L 27/50 623/8 |
| 2010/0222880 A1* | 9/2010 | Muscat ..................... A61F 2/52 623/7 |
| 2011/0082547 A1* | 4/2011 | Corbitt, Jr. ................ A61F 2/12 623/8 |
| 2011/0144748 A1 | 6/2011 | Chang et al. |
| 2012/0179251 A1* | 7/2012 | Corbitt, Jr. ............ A61F 2/0059 623/8 |
| 2012/0302874 A1 | 11/2012 | Hollstien |
| 2014/0050689 A1* | 2/2014 | Pathak ................... A61K 35/12 424/78.3 |
| 2014/0112559 A1* | 4/2014 | Freeman .............. A61B 5/0059 382/128 |
| 2014/0142696 A1* | 5/2014 | Corbitt, Jr. ............ A61F 2/0059 623/8 |

(Continued)

FOREIGN PATENT DOCUMENTS

| WO | WO 2005/051444 A2 | 6/2005 |
| WO | 20160205468 A1 | 12/2016 |

OTHER PUBLICATIONS

Fairchild, Mark D., "Color Appearance Models: CIECAM02 and Beyond", IS&T/SID 12$^{th}$ Color Imaging Conference, Nov. 9, 2004.

(Continued)

*Primary Examiner* — Suzette J Gherbi

(57) ABSTRACT

An implantable device includes a hollow biocompatible shell and filling material. The shell is configured to be implanted in an organ of a patient. The filling material is configured to fill the shell so as to assume a specified shape of the implantable device, and is visually distinguished from tissue of the organ that surrounds the implantable device.

15 Claims, 3 Drawing Sheets

(56) References Cited

U.S. PATENT DOCUMENTS

2014/0206839 A1* 7/2014 Altman .............. A61K 38/1767
530/327
2015/0073473 A1* 3/2015 Broom ............... A61B 17/0469
606/228
2015/0297798 A1* 10/2015 Badylak .................. A61L 31/06
600/37

OTHER PUBLICATIONS

European Patent Office, Extended European Search Report, European Patent Application No. 16205808.5, dated Jan. 30, 2017, 10 pages.

* cited by examiner

COLORED SILICONE FOR IMPLANT SAFETY

FIELD OF THE INVENTION

The present invention relates generally to breast implants, and specifically to breast implants having improved safety.

BACKGROUND OF THE INVENTION

Various types of implants, such as breast implants, are used in a variety of therapeutic and cosmetic applications. Examples of prior art techniques are provided below.

PCT Patent application WO 2005/051444, whose disclosure is incorporated herein by reference, describes a device useful for reconstructing soft tissue, e.g., breast, chin, lip, nasal, cheek and autogenous tissue, comprises soft tissue implant and either anti-scarring agent or composition comprising anti-scarring agent.

U.S. Pat. No. 7,736,391, whose disclosure is incorporated herein by reference, describes a prosthesis for implant in a human patient body. The prosthesis has an external envelope, at least one implant filling material, and at least one biologically compatible rupture indicator encapsulated in a sustained release delivery vehicle and disposed in a carrier medium. The rupture indicator is capable of leaking out of upon rupture of the external envelope, and triggering a signal that is detectable by the patient as it is released from the delivery vehicle, allowing for detection of a rupture or impending rupture by the patient.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention that is described herein provides an implantable device including a hollow biocompatible shell and filling material. The shell is configured to be implanted in an organ of a patient. The filling material is configured to fill the shell so as to assume a specified shape of the implantable device, and is visually distinguished from tissue of the organ that surrounds the implantable device.

In some embodiments, the filling material differs in color from the tissue by at least a predefined hue difference. In other embodiments, the predefined hue difference is four degrees in accordance with a red-green-blue (RGB) hue scale. In an embodiment, the tissue has a first color having a first dominant wavelength, and the filling material has a second color having a second dominant wavelength, which differs from the first wavelength by at least a predefined wavelength difference. In an example embodiment, the predefined wavelength difference is 50 nm.

In some embodiments, the filling material includes a fluorescent tracer that is adapted to glow when illuminated with light having a color selected from a list consisting of blue and ultra-violet (UV). In other embodiments, the filling material is configured to shape a size and a contour of the organ. In yet other embodiments, the filling material includes silicone gel.

In an embodiment, the filling material includes carbon black, which is configured to set a color of the filling material to black. In another embodiment, the filling material includes barium sulfate, which is configured to set a color of the filling material to white.

There is additionally provided, in accordance with an embodiment of the present invention, a method for producing an implantable device including providing a hollow biocompatible shell, configured to be implanted in an organ of a patient. The shell is filled with filling material, which is configured to assume a specified shape of the implantable device, and which is visually distinguished from tissue of the organ that surrounds the implantable device.

There is further provided, in accordance with an embodiment of the present invention, a method for removing residues of a ruptured implantable device. The method includes identifying in an organ of a patient a rupture of an implantable device. The device includes a hollow biocompatible shell, and filling material that is configured to fill the shell so as to assume a specified shape of the implantable device and is visually distinguished from tissue of the organ that surround the implantable device. The organ is imaged so as to detect residues of the filling material that are visually distinguished from tissue, and residues are removed from the organ.

The present disclosure will be more fully understood from the following detailed description of the embodiments thereof, taken together with the drawings, in which:

DETAILED DESCRIPTION OF EMBODIMENTS

Overview

Figure 1:
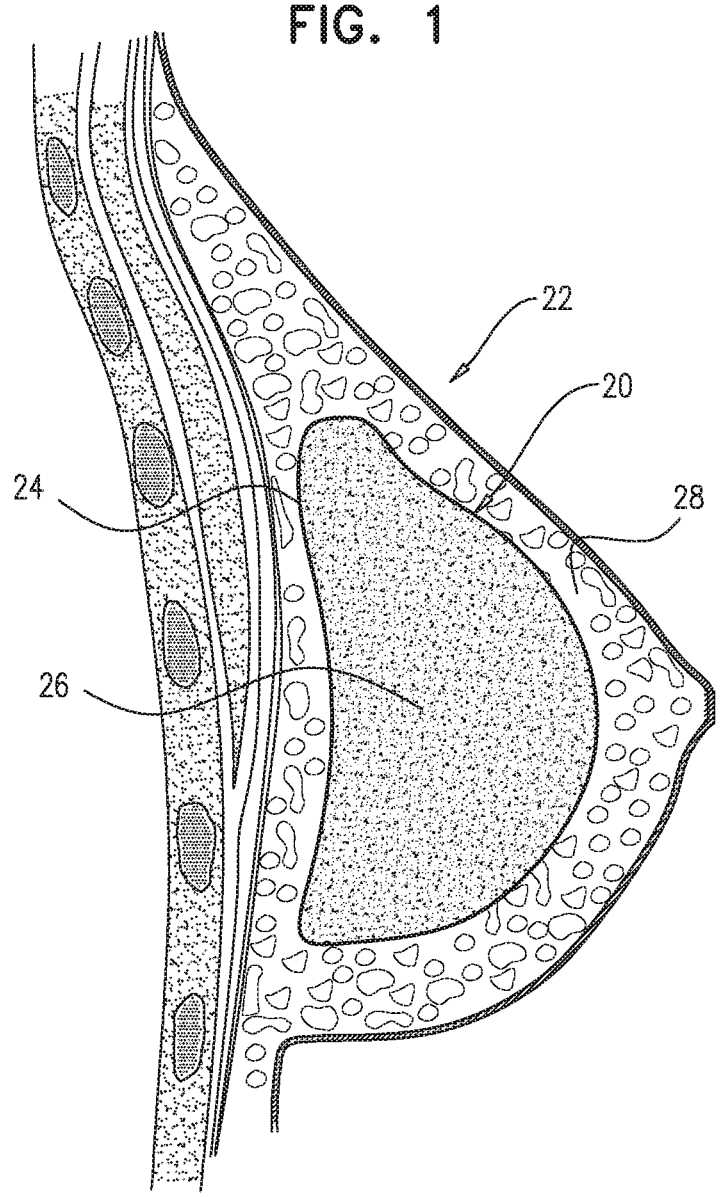
FIGS. 1 and 2 are schematic pictorial illustrations of a breast implant, in accordance with an embodiment of the present invention.

Medical implants, such as breast implants, are typically used for reconstructing a human breast after excision or for shaping the size and contour of breasts in cosmetic applications. A breast implant typically comprises a filling material, also known as implantable material, such as silicone gel that conforms to the texture of natural tissue of the breast (e.g., fat or muscle tissue). The implant further comprises a biocompatible shell adapted to encapsulate the implantable material and to be implanted in the human breast. The shell typically comprises a soft and flexible material that has no physical or chemical interactions with the surrounding tissue. The shell is designed to conform to the texture of the tissue, and undesirably has limited durability against punctures.

In an event of a puncture, the ruptured breast implant must be removed from the breast in a chirurgical procedure so as to prevent leakage of silicone gel from the implant to the surrounding tissue. In many events of ruptured implants, at least some of the silicone gel spills out of the ruptured shell and diffuses into the tissue around the puncture. The contact of silicone gel with the tissue may cause medical complications.

In conventional breast implants, the color and texture of the silicone gel that leaks out of the ruptured implant typically resembles the color and texture of the surrounding tissue. A surgeon that carries out a breast surgery to remove a punctured implant may therefore face difficulty in distinguishing between the human tissue and the gel, and therefore may fail to remove all the residual gel, or scar the surrounding tissue of the breast.

Embodiments of the present invention that are described herein provide techniques for safe removal of the breast implant by incorporating in the implant shell a filling material that is visually distinguishable from the surrounding tissue. The disclosed techniques improve the visual contrast between the filling material and the surrounding tissue, and thus enable complete removal of filling-material residues during or after removal of the ruptured implant.

In an embodiment, the color of the filling material is by itself distinguishable from the surrounding tissue. In another embodiment, one or more additive colorant materials are mixed with the silicone gel so as to form a filling material whose color differs from the color of the surrounding tissue. For example, a carbon black additive changes the color of the silicone gel to black, thus the carbon turns the gel color from clear to a color different from the surrounding natural fat. In yet another embodiment, the gel may be mixed with a fluorescent tracer so that the mixture glows in the presence of blue or ultra-violet (UV) light.

In some embodiments, further to the removal of the implant, a minimally invasive laparoscopic procedure may be carried out for removing the leaked filling-material residues. During the procedure, the surgeon may insert a catheter, which comprises a camera and a suction head, into the breast. The camera may operate with visible light (e.g., in case of using colorant additives) or under UV or blue illumination (e.g., in case the gel is mixed with a fluorescent tracer), so as to detect residues of the filling material and to remove these residues using the suction head.

The disclosed techniques improve patient safety by eliminating residues of potentially unhealthy materials from the body after removal of ruptured implants. In addition, these techniques reduce redundant internal scars to the tissue around the former location of the implant, and result in smaller external scars to the skin. Furthermore, the disclosed techniques reduce the level of trauma involved in the implant removal procedure, and reduce pain caused to the patient. Finally, the ability to accelerate the isolation of silicone gel residues, saves operating room (OR) resources, such as surgeon time, OR time and amounts of irrigation and therapeutic fluids consumed, thus reducing the costs of such procedures.

Implant Description

FIG. 1 is a schematic pictorial illustration of a breast implant 20 implanted into a women's breast 22, in accordance with an embodiment of the present invention.

Breast 22 comprises natural tissue 28 surrounding implant 20, which is a prosthesis used to shape the size and contour of breast 22. Implant 20 comprises a shell 24 encapsulating gel 26, which is a filling material made of soft material to imitate the texture of tissue 28. The gel is adapted to shape the size and contour of breast 22. Gel 26 may comprise silicone gel or any other suitable filling material for shaping breast 22.

In some embodiments, the color of the filling material is by itself distinguishable from the color of the surrounding breast tissue. In other embodiments, an additive colorant material (not shown) is mixed with gel 26 so as to change the color of gel 26 to a color that is distinguishable from the breast tissue color. In an embodiment, the colorant material may comprise carbon black, so as to turn the color of gel 26 into black (or dark gray according to the amount of additive used). In another embodiment, the colorant may comprise barium sulfate that turns the color of gel 26 into milky white.

The term "distinguishable color" or "visually distinguished" may be quantified, for example, using a red-green-blue (RGB) hue scale. Hue is a set of color appearance parameters, defined technically, for example, by Mark Fairchild, in "Color Appearance Models: CIECAM02 and Beyond," IS&T/SID 12$^{th}$ Color Imaging Conference, Springfield, Va., 2004, which is incorporated herein by reference.

Hue may be defined as an angular value on a polar scale that spans the entire color range of visible-light. In an embodiment, a predefined difference between two hue angles may be used as a measure of difference between two colors. A human eye can distinguish up to a few hundred hues, however the sensitivity of the human eye may change across the spectrum. For example, the sensitivity for green hues is typically higher than for yellow. Dividing the hue scale (360 degrees) by 100 hues results in a safe distinguishable value of 3.6 degrees.

Thus, in an embodiment, a difference of 4 degrees or more between the hue angle of gel 26 and the hue angle of the surrounding tissue is regarded as "visually distinguished." In another embodiment, a more conservative hue difference of 10 degrees or more is regarded as "visually distinguished." Further alternatively, other suitable hue differences can also be used.

Alternatively, a scale of the spectrum visible to a typical human eye (e.g., wavelengths in the range 390-700 nm) may be used to measure the color difference. For example, to be "visually distinguished," the dominant wavelength in the color of the filling material (e.g., measured by a spectrometer) may be specified to differ from the dominant wavelength in the color of the surrounding tissue by at least 50 nm. In another embodiment, other suitable differences in the dominant wavelength can be used.

In yet other embodiments, gel 26 may be mixed with a bio-compatible fluorescent tracer (not shown) such as dextrans, fluorescent nanoparticles. The mixture of gel 26 and fluorescent tracer is configured to glow in the presence of blue or ultra-violet (UV) illumination.

Using Colored Silicone for Implant Safety

Shaping implants, such as breast implants, are designed to be biocompatible and safe. Shell 24 typically comprises materials that do not interact with or irritate the surrounding tissue. Shell 24 is configured to encapsulate gel 26 so as to prevent direct contact between gel 26 and tissue 28. After implantation, during daily human activities and over time, shell 24 may age or be damaged by injury caused to breast 22, e.g., by a sharp object, high impact, or due to any other reason.

As a result, shell 24 may rupture and silicone gel 26 may leak out of implant 20 to surrounding tissue 28. The leakage of gel 26 that comes into contact with tissue 28 could endanger the patient's health. Thus, the damaged implant and any residues of silicone gel 26 should be removed from breast 22 promptly.

In the disclosed embodiments, the filling material of the implant is visually distinguishable from the surrounding tissue, which enables complete removal of the gel residues. Complete removal of the gel residues is essential, because contact of the gel material with tissue 28 of breast 22 for long periods may cause medical complications.

Figure 2:
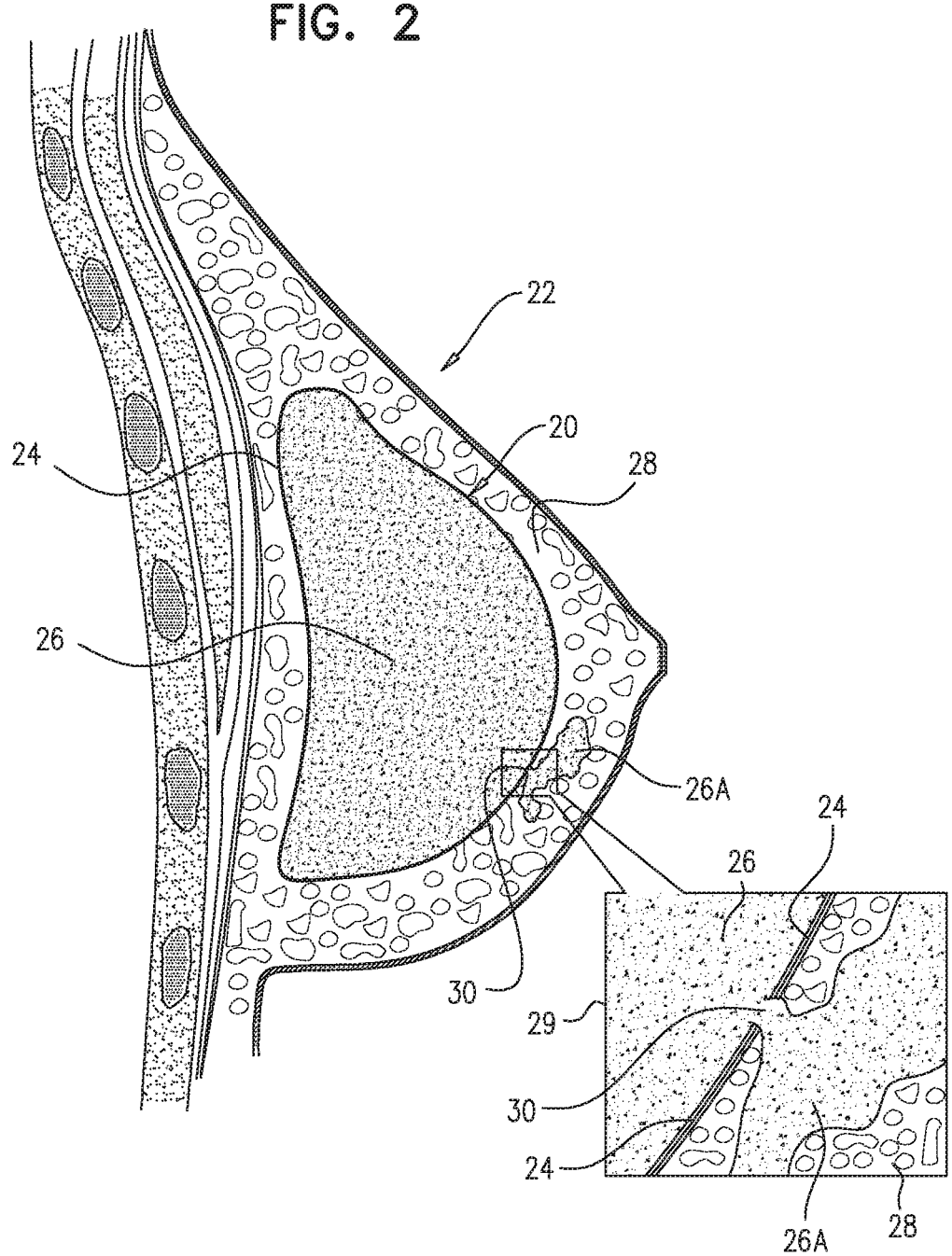

FIG. 2 is a schematic pictorial illustration of a ruptured breast implant 20 in a women's breast 22, in accordance with an embodiment of the present invention. Implant 20 is ruptured at the lower right area, causing leakage of gel out of the implant. Referring to an inset 29, a rupture 30 in shell 24 causes leakage of gel 26A from implant 20 into tissue 28. Gel 26A is substantially identical in composition to gel 26 and denoted 26A to mark the portion of gel 26 that has leaked out of the implant into tissue 28.

Gel 26A that has leaked out is in direct contact with tissue 28, in some embodiments the gel comprises the additive colorant material as described in FIG. 1. As shown in FIG. 2 (and in greater detail, in inset 29) the color of gel 26A differs from the color tissue 28. In an embodiment, the colored gel can be identified during surgery, after cutting through breast 22 and exposing the respective area to visible light. In another embodiment, by inserting a minimally-invasive camera, surgeon 44 may identify the colored gel in a visible light. For example, the color of natural tissue 28 is seen as light gray and the color of gel 26A mixed with carbon black is seen to be black or dark gray.

In other embodiments, gel 26A may comprise a fluorescent tracer. Surgeon 44 may apply blue or UV light to distinguish between gel 26A and tissue 28, in an embodiment, the gel mixed with the fluorescent tracer glows in the presence of the blue or UV light.

In another embodiment, the gel glows after cutting through breast 22 and exposing the respective area to external blue or UV light. In an alternative embodiment, the surgeon may use a minimally-invasive camera that comprises internal blue or UV illumination so that gel 26A glows, in contrast to tissue 28 (or any other tissue in breast 22) that remains dark.

Figure 3:
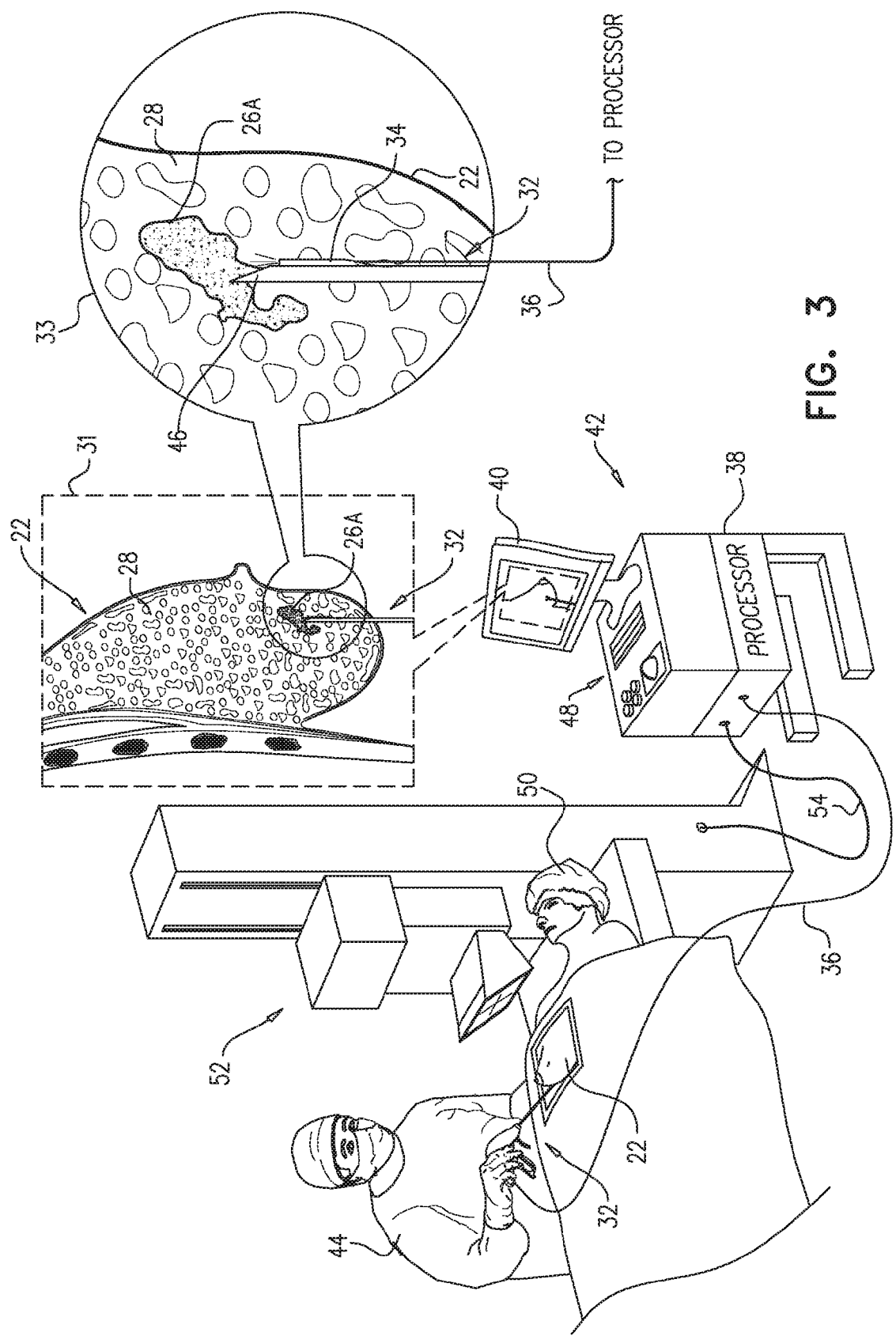
FIG. 3 is a schematic pictorial illustration of a procedure for visualization and removal of silicone gel residues from a human breast, in accordance with an embodiment of the present invention.

FIG. 3 is a schematic pictorial illustration of a procedure for visualization and removal of residues of silicone gel 26A from a human breast 22, in accordance with an embodiment of the present invention. In response to detecting a punctured implant 20, surgeon 44 removes the ruptured implant using any suitable removal procedure known in the art, and checks for residues of gel 26A in breast 22.

In the example of FIG. 3, surgeon 44 inserts a laparoscopic catheter 32 into breast 22 of a patient 50. Referring to an inset 33, in an embodiment, catheter 32 may comprise a minimally-invasive camera 34 attached to a suction head 46. In another embodiment, two separate catheters may be used, a first catheter for imaging and a second catheter for suction or for any other operating activity. Camera 34 is configured to illuminate the area in question, and to acquire video images that may display tissue 28 and residues of gel 26A.

Camera 34 transmits the images (i.e., video frames), via cables 36, to a computer system 42. In an embodiment, system 42 comprises a processor 38, which is configured to process the raw video signals and to present real time (RT) video images of the area in question on a screen 40. In another embodiment, surgeon 44 may use input devices and processor 38 to control, via cables 54, an external illumination system 52. In some embodiments, the external illumination system may comprise visible light illumination. In other embodiments, system 52 may comprise blue or UV light illumination in conjunction with, or instead of, the visible light illumination. In yet alternative embodiments, system 52 may comprise a camera (not shown) that provides surgeon 44 with a complete image of breast 22 during the procedure.

Referring to an inset 31, surgeon 44 inserts catheter 32 into breast 22. As shown in inset 31, the implant has already been removed from breast 22. In an embodiment, processor 38 is configured to present on screen 40 an augmented image of breast 22. The augmented image comprises an overlay of the complete image from system 52 and the internal video images acquired by camera 34. In the example of FIG. 3, breast 22 contains residues of gel 26A.

As described in the respective embodiments of FIGS. 1 and 2, the color of gel 26A is distinguishable from the color of tissue 28 and surgeon 44 may easily identify the gel residues and remove them using catheter 32 (as shown in inset 33). In some embodiments, system 52 may use visible light to provide surgeon with a complete image of breast 22. Camera 34 may use UV light to provide an overlay image of gel 26A glowing in the respective location within breast 22.

In other embodiments, processor 38 receives a location of catheter 32 from a position tracking system (not shown) and may synchronize the two images so as to create the augmented image of gel 26A within breast 22. In yet alternative embodiments, surgeon 44 may cut breast and use surgery techniques, other than minimally invasive techniques, to remove gel 26A. The procedure may be carried out in the presence of visible light (using colorants such as carbon black or barium sulfate) or in the presence of blue or UV light.

Processor 38 typically comprises a general-purpose processor, which is programmed in software to carry out the functions described herein. The software may be downloaded to the computer in an electronic form, over a network, for example, or it may, alternatively or additionally, be provided and/or stored on non-transitory tangible media, such as magnetic, optical, or electronic memory.

FIGS. 1-3 show a procedure for identifying the residues of gel 26A within breast 22, and removing the gel residues safely without removing portions of tissue or any other tissue of breast 22. The embodiments described herein can be used in other applications that involve implanting prostheses in any respective organ, such as calf, gluteal, or facial prostheses.

The implant material may comprise silicone gel or any other suitable material such as silicone rubber. The additive colorants and fluorescent tracers described in FIGS. 1-3 are depicted purely by way of example. In alternative embodiments, gel 26 may comprise any other suitable material or may be mixed with any suitable marker/tracer material that may assist to distinguish between gel 26A and the surrounding tissue of the respective organ. For example, when the organ comprises high density of blood vessels, the respective area may be naturally colored in red due to a massive bleeding during a removal procedure. Thus, the selected colorant of gel 26 may be white (e.g., using barium sulfate) or have any other suitable color that is significantly different from red (or dark red if the blood is deoxygenated).

In addition, the additive colorant may be used to distinguish between gel 26A and the surrounding tissue with certain medical imaging technologies, including non-invasive imaging techniques. For example, the additive colorant barium sulfate is radiopaque and can differentiated from the surrounding tissue in the presence of X-RAY radiation, such as in fluoroscopic imaging techniques or in computerized tomography (CT). Furthermore, the present techniques are not limited to breast implants and may be applied to implants intended for use in any suitable organ of a patient.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. An implantable device, comprising:
   a hollow biocompatible shell, configured to be implanted in an organ of a patient; and
   filling material, which is configured to fill the shell so as to assume a specified shape of the implantable device, and which is visually distinguished from tissue of the organ that surrounds the implantable device;
      wherein the filling material differs in color from the tissue by at least a predefined hue difference, the predefined hue difference is 4 degrees in accordance with a red-green-blue (RGB) hue scale.

2. The implantable device according to claim 1, wherein the tissue has a first color having a first dominant wavelength, and wherein the filling material has a second color having a second dominant wavelength, which differs from the first wavelength by at least a predefined wavelength difference.

3. The implantable device according to claim 2, wherein the predefined wavelength difference is 50 nm.

4. The implantable device according to claim 1, wherein the filling material comprises a fluorescent tracer that is adapted to glow when illuminated with light having a color selected from a list consisting of blue and ultra-violet (UV).

5. The implantable device according to claim 1, wherein the filling material comprises silicone gel.

6. The implantable device according to claim 1, wherein the filling material comprises carbon black, which is configured to set a color of the filling material to black.

7. The implantable device according to claim 1, wherein the filling material comprises barium sulfate, which is configured to set a color of the filling material to white.

8. A method for producing an implantable device, comprising:
   providing a hollow biocompatible shell, configured to be implanted in an organ of a patient; and
   filling the shell with a filling material, which is configured to assume a specified shape of the implantable device, and which is visually distinguished from tissue of the organ that surrounds the implantable device;
      wherein the filling material differs in color from the tissue by at least a predefined hue difference, the predefined hue difference is 4 degrees in accordance with a red-green-blue (RGB) hue scale.

9. The method according to claim 8, wherein the tissue has a first color having a first dominant wavelength, and wherein the filling material has a second color having a second dominant wavelength, which differs from the first wavelength by at least a predefined wavelength difference.

10. The method according to claim 9, wherein the predefined wavelength difference is 50 nm.

11. The method according to claim 8, wherein the filling material comprises silicone gel.

12. The method according to claim 8, wherein the filling material comprises a fluorescent tracer that is adapted to glow when illuminated with light having a color selected from a list consisting of blue and ultra-violet (UV).

13. The method according to claim 8, wherein the filling material is configured to shape a size and a contour of the organ.

14. A method for removing residues of a ruptured implantable device, the method comprising:
   identifying in an organ of a patient a rupture of an implantable device, the device comprising:
      a hollow biocompatible shell; and
      filling material, which is configured to fill the shell so as to assume a specified shape of the implantable device, and which is visually distinguished from tissue of the organ that surround the implantable device;
   imaging the organ so as to detect residues of the filling material that are visually distinguished from tissue; and
   removing the residues from the organ;
      wherein the filling material comprises a fluorescent tracer that is adapted to glow when illuminated with light having a color selected from a list consisting of blue and ultra-violet (UV), and wherein imaging the organ comprises illuminating the organ with the light.

15. The method according to claim 14, wherein imaging the organ comprises applying a minimal invasive imaging procedure.

* * * * *